United States Patent [19]

Sellers

[11] 4,290,756
[45] Sep. 22, 1981

[54] DENTAL TWIST-LOCK PIN AND DRILL

[76] Inventor: Wm. Ralph Sellers, 717 Moorside, San Antonio, Tex. 78239

[21] Appl. No.: 51,317

[22] Filed: Jun. 22, 1979

[51] Int. Cl.³ .............................................. A61C 5/04
[52] U.S. Cl. ................................................... 433/225
[58] Field of Search ....................... 433/225, 228, 174; 85/41, 46; 128/92 C; 3/1

[56] References Cited

U.S. PATENT DOCUMENTS

| 275,491 | 4/1883 | How | 433/220 |
| 616,302 | 12/1898 | Evans | 433/220 |
| 2,075,024 | 3/1937 | Delano | 285/40 |
| 3,672,058 | 6/1972 | Nikoghossian | 433/174 |
| 4,060,896 | 12/1977 | Wahnish | 433/174 |
| 4,103,422 | 8/1978 | Weiss | 433/174 |

FOREIGN PATENT DOCUMENTS 2395738 3/1979 Fed. Rep. of Germany ...... 433/174
910726 8/1951 France .

*Primary Examiner*—Robert Peshock
*Attorney, Agent, or Firm*—Donald J. Singer; Arsen Tashjian

[57] ABSTRACT

A twist-lock pin for improving the retention and resistance characteristics of plastic dental restorative materials and a drill for drilling a tapered hole into sound tooth structure whereupon the geometrically similar but oversized left-hand threaded pin is inserted. Slight rotation of the pin in a counter-clockwise manner causes the threads to bite simultaneously, effectively locking it into place. Plastic restorative materials including dental amalgam, composites, silicates, resins and gold foil may be inserted against the threaded protruding portion of the pin to enhance the retention and resistance characteristics.

2 Claims, 2 Drawing Figures

DENTAL TWIST-LOCK PIN AND DRILL

STATEMENT OF GOVERNMENT INTEREST

The invention described herein may be manufactured and used by or for the Government for governmental purposes without the payment of any royalty thereon.

REFERENCE TO RELATED PATENT APPLICATION

Reference is made to my copending patent application, Ser. No. 51,316 filed on even date herewith which describes and claims a wrench for use in inserting the twist-look pin described herein into the tooth.

BACKGROUND OF THE INVENTION

This invention relates to a twist-lock pin and tapered drill for improving the retention and resistance characteristics of plastic dental restorative materials and, more particularly, the invention is concerned with providing a tapered left-hand threaded pin for insertion into a hole in a tooth drilled with a geometrically similar drill bit. Slight rotation of the pin in a counter-clockwise direction causes the threads to bite simultaneously, effectively locking the pin into place.

Heretofore, it has been the common practice to anchor a superstructure to the understructure of a tooth by drilling one or more holes into the tooth or understructure. A pin or rod is inserted in each of the holes and allowed to extend above the understructure so that the exposed portion of the pin may be used to anchor the superstructure onto the tooth. The pins are relatively small in diameter and difficult to handle. It is especially difficult to insert the pin in the hole where the hole is undersized and the pin is threaded. An example of a prior art device is described in U.S. Pat. No. 3,434,209 and is manufactured and distributed by Whaledent International of New York, N.Y. In this prior art device called the T.M.S. system, the pin requires ten complete revolutions to seat a distance of 2 mm. Also, the tool for inserting the T.M.S. pin is a slotted screwdriver design which does not hold the pin securely causing problems during initial pin insertion. This can lead to unwanted pin shear and uneven stress loading of the tooth structure if the pin is not in exact alignment in the hole.

What is needed is a dental anchor pin which can be easily inserted into the opening in the tooth with a minimum of rotation being required. The pin should be easier to align in the tooth opening with position control of the pin during insertion. Also, the rate of loading of the pin should be more rapid than presently available pins in order to provide the operator with greater "feel" and ability to forecast and prevent ultimate torsion failure.

The hereinafter described twist-lock pin and drill disclose a system which will provide all of the desired features noted above. The pin is easier to insert since the tip of the pin is smaller than the surface diameter of the pinhole in the tooth. The pin seats in a counter-clockwise rotation and less than 360° rotation is required to fully seat the pin in the tooth opening. Also, because of the counter-clockwise rotation of the pin, the action of the cut-off bur which rotates clockwise, serves to seat the pin deeper and more securely in the tooth rather than loosen it when the excess portion of the pin is reduced.

SUMMARY OF THE INVENTION

The present invention is concerned with providing a twist-lock pin and drill for improving the retention and resistance characteristics of plastic dental restorative materials. A tapered hole is drilled into sound tooth structure whereupon a geometrically similar, but oversized, threaded pin is inserted. Slight rotation of the pin in a counter-clockwise manner causes the threads to bite simultaneously, effectively locking it into place. Plastic restorative materials, such as dental amalgam, composites, silicates, resin and gold foil may be inserted against the threaded protruding portion of the pin, thus enhancing its retention end resistance characteristics.

Accordingly, it is an object of the invention to provide a dental twist-lock pin and drill wherein the pin is taper fitted into a geometrically similar but undersized hole allowing all threads to bite simultaneously and requiring less than 360° rotation to fully seat.

Another object of the invention is to provide a dental twist-lock pin and drill system wherein the pin includes a left-hand thread and seats with counter-clockwise rotation so that the action of a clockwise rotating bur which may be used to reduce excess, only tends to seat the pin deeper rather than unscrew it.

Still another object of the invention is to provide a dental twist-lock pin and drill arrangement wherein all threads bite simultaneously so that the stresses are evenly distributed to surrounding tooth structure.

A further object of the invention is to provide a dental twist-lock pin threaded for insertion into a tooth drilled with a geometrically similar drill to form a tapered hole. The pin self aligns in the tapered hole and employs double lead screws to increase thread area.

A still further object of the invention is to provide a dental twist-lock tapered pin and drill wherein the time necessary for insertion into the tooth is reduced because less screwing is required and the tip of the pin is small relative to the surface diameter of the pin hole.

Another still further object of the invention is to provide a dental twist-lock pin and drill system whereby the rate of loading as perceived by the operator is more rapid than conventional non-tapered pins, providing the operator with greater "feel" and ability to forecast ultimate torsion failure.

These and other objects, features and advantages will become more apparent after considering the following detailed description taken in conjunction with the annexed drawing and appended claims.

DESCRIPTION OF A PREFERRED EMBODIMENT

Figure 1:
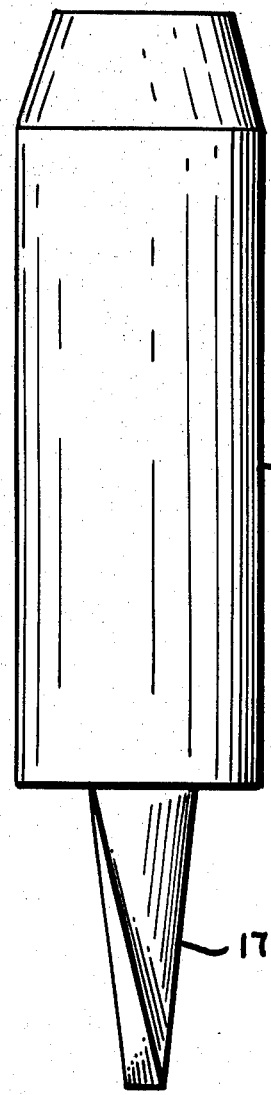
FIG. 1 is a side view of a drill of the type used in the preparation of a tooth for practicing the invention.
Figure 2:
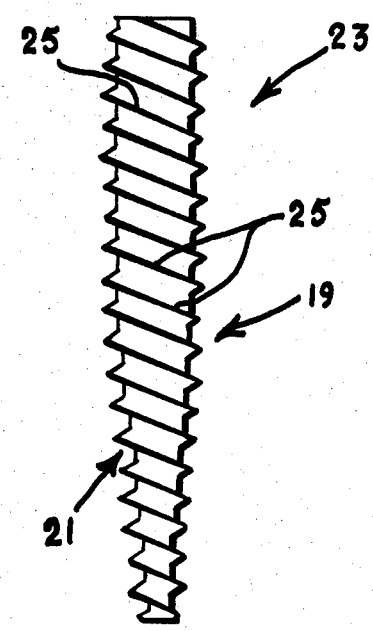
FIG. 2 is a side view of a twist-lock dental pin according to the invention for insertion into the opening made by the drill of FIG. 1.

Referring now to the drawings, there is shown in FIG. 1 a drill 13 including a shank portion 15 and a tapered cutting end 17. The drill 13 is adaptable for use with any standard holder and the tapered end 17 is used to drill a tapered hole into sound tooth structure.

A threaded pin 19 including a lower tapered portion 21 which is geometrically similar to the tapered end 17 of the drill 13 and a straight untapered upper portion 23 is inserted into the hole in the tooth made by the drill 13.

The lower portion 21 of the pin 19 is slightly oversized so as to be a tight fit in the hole in the tooth made by the drill 13. The pin 19 includes a number of threads 25 along the length thereof for gripping the sides of the tapered hole in the tooth and effectively locking it into place. The threads 25 are preferably left-hand so that rotation in the counter-clockwise direction will cause the pin 19 to seat firmly in the drilled hole. Since the lower portion 21 of the pin 19 is tapered, only a slight rotation in the counter-clockwise direction will cause the pin 19 to seat firmly in the drilled hole. Since the lower portion 21 of the pin 19 is tapered, only a slight rotation in the counter-clockwise direction will lock it into place. Plastic restorative materials such as dental amalgam, composites, silicates, resins and gold foil, may be inserted against the straight threaded protruding portion 23 of the pin 19, thus enhancing its retention and resistance characteristics.

The twist-lock tapered pin 19 differs from existing pin designs in that both the pin and pin-hole are tapered. This allows the pin 19 to freely enter the pin-hole for approximately 75% of its depth before rotation is begun. The design of the thread 25 includes an extremely steep pitch to produce rapid seating of the pin 19. In order to increase the thread area available for retention, two sets of threads are used which are parallel and independent forming double lead screw threads. All other threaded pins employ a single continuous thread of lesser pitch.

A wrench which allows precise control over the pin 19 during insertion is described in detail in my copending patent application Ser. No. 51,316. The wrench holds the pin 19 which self aligns in the tapered channel in the tooth and the wrench is removed after the pin 19 is seated in the tooth. Since the pin 19 is rotated into place in a counter-clockwise direction, it is not loosened by cutting off part of its protruding section with a clockwise revolving bur.

Although the invention has been illustrated in the foregoing specification in terms of a preferred embodiment thereof, the invention is not limited to this embodiment or to the particular configuration shown and described. It will be apparent to those skilled in the art that certain changes, modifications and substitutions can be made with respect to the shape of the elements without departing from the true spirit and scope of the appended claims. It can be seen that the invention may be used in the same manner that conventional bonded, threaded, and cemented pins are used to enhance the retention characteristics of plastic dental restoration material and tooth structure.

Having thus set forth the nature of my invention, what I claim as new and desire to secure by Letters Patent of the United States is:

1. In combination, a tapered drill for drilling a tapered hole into sound tooth structure and a twist-lock pin for insertion into the hole drilled by the tapered drill, said twist-lock pin having a left hand thread on the outer surface thereof, said twist-lock pin having a tapered lower portion and a straight threaded upper portion for threadable engagement with a suitable insertion wrench, the tapered lower portion of said twist-lock pin being dimensioned to be fully insertable into the tapered hole in the tooth without threading for engagement with the entire tapered surface of the drilled hole in the tooth, the twist-lock pin being positively held in the wrench and inserted into the tapered drilled hole and rotated counter-clockwise less than one revolution thereby causing the pin to be fully seated in the tooth.

2. The combination defined in claim 1 wherein the threaded outer surface of said twist-lock pin includes two sets of parallel and independent left-hand threads forming double lead screw threads thereby increasing the thread area available for retention.

* * * * *